United States Patent [19]

Edwards

[11] Patent Number: 4,532,135

[45] Date of Patent: Jul. 30, 1985

[54] RENOPROTECTIVE TREATMENTS EMPLOYING VASODILATOR COMPOUNDS

[76] Inventor: K. David G. Edwards, New York, N.Y.

[21] Appl. No.: 424,076

[22] Filed: Sep. 27, 1982

Related U.S. Application Data

[63] Continuation-in-part of Ser. No. 232,650, Feb. 19, 1981, Pat. No. 4,361,564, which is a continuation-in-part of Ser. No. 965,059, Nov. 30, 1978, Pat. No. 4,250,191.

[51] Int. Cl.$^3$ .................. A61K 31/54; A61K 31/135; A61K 31/415; A61K 31/445; A61K 31/475; A61K 31/495; A61K 31/505
[52] U.S. Cl. ..................... 514/222; 514/248; 514/259; 514/400; 514/401; 514/646; 514/929
[58] Field of Search .................. 424/251, 273 R, 246, 424/330, 267, 262, 250

[56] References Cited

U.S. PATENT DOCUMENTS

| | | | |
|---|---|---|---|
| 3,969,508 | 7/1976 | DiTullio et al. | 424/275 |
| 4,130,647 | 12/1978 | Taylor | 424/251 |
| 4,255,432 | 3/1981 | Kluge et al. | 424/267 |
| 4,377,581 | 3/1983 | Hess et al. | 424/251 |

OTHER PUBLICATIONS

Merck Index, 10th Ed., pp. 516–517, 1983.
Drugs of the Future, 7: 877, (1982).
Drugs of the Future, 3: 721–722, (1978).
Drugs of the Future, 6: 751–752, (1981).
Kirkendull et al., JAMA, vol. 240, No. 23, pp. 2553–2556, 12/1/78.
Griffiths et al., USAN and the USP Dictionary of Drug Names, (1980), pp. 121, 145, 245, 292, 293, 388, 389.
The Merck Index, 9th Ed., (1976), p. 9764.

*Primary Examiner*—Allen J. Robinson
*Attorney, Agent, or Firm*—Natter & Natter

[57] ABSTRACT

A treatment method and substances have been found to reduce the risk of incurring renal damage or failure. Vasodilators useful for the treatment of hypertension have been found to lower cholesterol levels and prevent renal failure or damage. These substances are administered alone or in combination with other substances useful in the treatment of hyperlipidemia such as phenoxyacetic acid derivatives. Suitable vasodilators include: hydralazine hydrochloride and functionally similar agents such as endralazine, trimazosin, minoxidil, and diazoxide; prazosin hydrochloride and functionally similar agents such as doxazosin, triodazosin, phentolamine hydrochloride, phenoxybenzamine hydrochloride, benextramine, indoramine, and yohimbine; clonidine HCl and functionally similar agents such as guanabenz, guanfacine, lofexidine, and UK No. 14,304; labetalol and other combined alpha and beta blocking agents such as prizidolol and peroxidil.

8 Claims, No Drawings

RENOPROTECTIVE TREATMENTS EMPLOYING VASODILATOR COMPOUNDS

RELATED APPLICATIONS

This application is a continuation in part of an application entitled Renoprotective Treatments Employing Vasodilator Compounds, Ser. No. 232,650, filed Feb. 19, 1981 and issued Nov. 30, 1982 as U.S. Pat. No. 4,361,564 which was a continuation in part of an application entitled Improvements in Preventing Renal Failure, Ser. No. 965,059, filed Nov. 30, 1978 and issued Feb. 10, 1981 as U.S. Pat. No. 4,250,191. The prior application (now U.S. Pat. No. 4,250,191) was directed to a method of preventing renal failure by administering an antihyperlipidemic substance comprising a phenoxyacetic acid derivative.

BACKGROUND OF THE INVENTION

1. Field of the Invention

The present invention relates generally to the treatment of renal conditions and more particularly to the prevention of renal failure through the administration of substances which have antihyperlipidemic characteristics.

2. Brief Description of the Prior Art

In the past, elevated serum cholesterol and triglyceride concentrations were considered as high risk factors together with cigarette smoking and hypertension for coronary artery disease. This was especially so when both lipid parameters were elevated simultaneously. Therefore, it was not surprising to find the exaggerated incidence of atherosclerosis and coronary heart disease in human nephrotic syndrome, the advanced stages of which were traditionally accompanied by high lipid levels.

As a countermeasure to coronary and vascular problems, it was suggested that antihyperlipidemic drugs be used. Indeed, recent studies indicate that the drug clofibrate gave significant protection against ischemic heart disease and death in patients with angina pectoris. Studies with patients who have undergone renal transplantation have also revealed that renal failure was usually accompanied by hypertriglyceridaemia. This condition was generally believed to be a secondary condition or complication of an existing renal damage.

Severe hypertension itself was considered as a high risk factor not only to coronary artery disease but in addition to renal diseases and cerebral hemorrhage. Treatment of severe hypertension with vasodilators has been effective in reducing the hypertensive condition which has resulted in a concomitant reduction in cardiac failure and cerebral hemorrhages in such patients.

SUMMARY OF THE INVENTION

As set forth in the related application, now U.S. Pat. No. 4,250,191 and incorporated herein by reference, substances useful in the treatment of hyperlipidemia have been found to reduce or prevent renal failure. It occurred to the inventor that the relationship between increased lipid levels and renal disease might serve to increase or aggravate renal disease associated with hypertension.

An experiment was proposed to feed a number of spontaneously hypertensive rats a diet which would encourage a hyperlipidemic condition. In some of these rats chronic renal disease was induced by injection of puromycin aminonucleoside. The hyperlipidemic rats experienced marked renal failure. Comparative tests with controls (hypertensive rats fed hypolipidemic diets) did not show this renal failure.

Some of the hypertensive rats were fed an antihyperlipidemic substance comprising a phenoxyacetic acid derivative (halofenate). These rats exhibited a reduced tendency to renal failure when injected with puromycin aminonucleoside.

Further rats were fed a vasodilator which is also an alpha-adrenergic receptor binding agent (hydralazine). These rats also exhibited a reduced tendency to renal failure when injected with puromycin aminonucleoside. Additional rats that were fed a combination of halofenate and hydralazine also indicated a reduced tendency to renal failure.

The vasodilator hydralazine not only provided antihypertensive results but also functioned as an antihyperlipidemic agent reducing the triglyceride and cholesterol levels. The reduction in cholesterol levels was more pronounced than the reduction in triglyceride levels.

It was concluded that vasodilators which are helpful in reducing hypertensive conditions also provide beneficial reduction in lipid levels thus reducing a risk factor in renal failure. Vasodilators could be administered as a protective or prophylactic treatment at the onset of the hyperlipidemic condition so as to prevent renal failure.

It is an object of the present invention to provide a method of reducing the risk of incurring the renal damage by prophylactic treatment with a vasodilator.

Another object of the present invention is to provide a new medical use for a vasodilator.

It is a further object of the present invention to administer a substance used in the treatment of hypertensive conditions as a prophylaxis against renal failure per se.

A further object of the present invention is to provide a method of reducing the risk of incurring renal failure by prophylactic treatment with a combination of substances including at least one vasodilator and one antihyperlipidemic agent.

A still further object of the present invention is to provide a method of reducing the risk of incurring renal damage by prophylactic treatment with at least one alpha-adrenergic receptor binding agent.

Other objects in part will be obvious and in part will be pointed out hereinafter.

With these ends in view, the invention finds embodiment in certain combinations of elements and arrangements of parts by which the said objects and certain other objects are hereinafter attained.

DESCRIPTION OF THE PREFERRED EMBODIMENT

In accordance with the invention, it is proposed to administer at least one antihyperlipidemic substance comprising a vasodilator to hosts as a protective or prophylactic treatment against renal failure. A preferred substance comprising hydralazine hydrochloride may be given in quantities of between 40 and 200 milligrams per day to human hosts.

With respect to hydralazine hydrochloride, this vasodilator has been prescribed as a hypotensive agent in dosages of up to 400 mg. per day. Hydralazine hydrochloride is also referred to as 1-Hydrazinophthalazine Hydrochoride which is shown by the following formula:

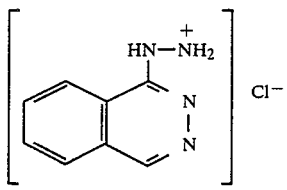

A further preferred vasodilator/alpha-adrenoceptor binding agent, prazosin hydrochloride, is a quinazoline derivative. Prazosin hydrochloride comprises the hydrochloride salt of 1-(4-amino-6,7-dimethoxy-2-quinazolinyl)-4-2(2-furoyl) piperazine and its structural formula is:

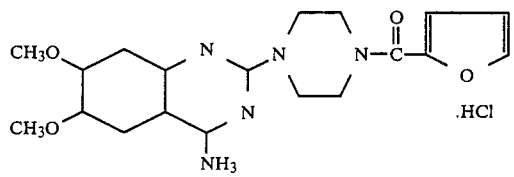

It has been employed in the treatment of hypertension in humans with a daily dosage of between 1 milligram and 40 milligrams. The dosage in patients with chronic renal failure will be reduced in proportion to the reduction in renal function.

A further well known vasodilator is clonidine hydrochloride which comprises an imidazoline derivative. Clonidine hydrochloride is also referred to as 2-(2,6-dichlorophenylamino)-2-imidazoline hydrochloride. It has been administered to adult humans for treatment of hypertension in dosages of 0.1 milligrams through 2.4 milligrams per day.

With respect to clonidine hydrochloride, it is believed that its mechanism of action appears to be the stimulation of vasodilation by binding to central postsynaptic alpha-receptors, while prazosin hydrochloride and hydralazine hydrochloride are believed to function by blocking peripheral postsynaptic alpha-adrenoceptors.

Other vasodilators which provide antihyperlipidemic effects including alpha-blocking agents and combined alpha and beta blocking agents are well suited for the treatment of renal conditions as a prophylaxis against renal failure pursuant to the present invention.

The use of hydralazine hydrochloride as a prophylaxis against renal failure was demonstrated to be statistically significant* (P less than 0.05) in the following tabulated test conducted over the course of one year with spontaneously hypertensive white female rats. The one year test was the equivalent to half of a lifespan of the rats and to approximately 30–35 years in man.

EXAMPLE

|  | Av. (n) | PTG | PTC | SBP | BW % | 2KW | Glmlscl (GS) SGS | + GGS | = FGS | Arteriolar Thg | Nec | Upr | BUN | GFR % |
|---|---|---|---|---|---|---|---|---|---|---|---|---|---|---|
| SLC/SHR | (5) | 493 | 99 | 138 | 131 | 1.58 | 0.2 | 0.1 | 0.3 | 0.3 | 0 | 9 | 26 | 94 |
| SLC/SHR + Hal | (8) | 158' | 63' | 132 | 117' | 1.48 | 0 | 0 | 0 | 0.1 | 0 | 9 | 20 | 122 |
| SLC/SHR + Hdz | (6) | 209' | 84 | 80' | 130 | 1.35 | 0 | 0 | 0 | 0 | 0 | 7 | 21 | 115 |
| SLC/SHR + Hdz + Hal | (8) | 218' | 50' | 81' | 118' | 1.41 | 0 | 0 | 0 | 0 | 0 | 11 | 29 | 82 |
| SLC/SHR + 1An | (8) | 387 | 215' | 166 | 119 | 2.59' | 1.7' | 2.7' | 4.4' | 2.8' | 1.1 | 85' | 97' | 25' |
| SLC/SHR + 1An + Hal | (8) | 263* | 98* | 134* | 117 | 1.81* | 1.2 | 0.8* | 2.0* | 0.9* | 0* | 44* | 28* | 85* |
| SLC/SHR + 1An + Hdz | (7) | 350 | 117* | 96* | 130 | 1.86* | 1.1 | 0.6* | 1.7* | 0.6* | 0* | 31* | 26* | 92* |
| SLC/SHR + 1An + Hdz + Hal | (8) | 247* | 82* | 89* | 119 | 1.67* | 0.8* | 0.6* | 1.4* | 0.4* | 0* | 38* | 35 | 69 |
| LC/SHR | (2) | 150 | 78 | 150 | 126 | 1.49 | 0.5 | 0 | 0.5 | 0 | 0 | 6 | 22 | 112 |
| LC/SHR + Hdz | (1) | 121 | 74 | 105 | 122 | 1.50 | 0 | 0 | 0 | 0.5 | 0 | 9 | 22 | 109 |
| LC/SHR + 1An | (2) | 256 | 124 | 132 | 127 | 1.83 | 2.0 | 1.0 | 3.0 | 0.5 | 0 | 50 | 25 | 96 |
| LC/SHR + 1An + Hdz | (2) | 140 | 83 | 125 | 132 | 1.73 | 0 | 0.2 | 0.2 | 0 | 0 | 32 | 22 | 109 |

SHR is a spontaneously hypertensive rat;

SLC is sucrose (60% or 45%)-lard (5% or 20%)-casein (21%)-cellulose (10%) rat food;

Hal is halofenate (0.05% of sucrose-lard diet) as a supplement;

Hdz is hydralazine hydrochloride, 80 mg. per liter of drinking water (4–6 mg/kg. per day ingested by the rats);

1An is 1 I.P.I. of puromycin aminonucleoside (90 (mg/kg);

LC is a lab chow cereal-based (fed to SHR controls);

PTG and PTC are plasma triglycerides and total cholesterol in mg/dl;

SBP is systolic blood pressure in mm Hg;

BW% is body weight as percent of initial weight;

2 KW is the weight of two kidneys in grams;

UPr is proteinuria/creatininuria, mg/mg;

BUN is blood urea-N, mg/dl;

GFR is glomerular filtration rate (% nornal=2400-/BUN).

The tabulated results of the example also indicate the renohistopathology evaluation by semiquantitation over a range of 0-4 +'s and the following were noted.

SGS is segmental glomerulosclerosis;
GGS is global glomerulosclerosis;
FGS is total focal glomerulosclerosis;
Thg is arteriolar thickening; and
Nec is arteriolar necrosis.

The above study established that hydralazine hydrochloride was effective in reducing the plasma total cholesterol (PTC) levels which were elevated by SLC diet and by chronic renal damage induced by puromycin aminonucleoside and was effective in reducing elevated plasma triglyceride levels induced by the sucrose-lard-casein diets (SLC). The study thus established that in addition to its known antihypertensive activity, the vasodilator hydralazine hydrochloride has significant antihyperlipidemic including antihypercholesterolemic activity.

The tabulated pathological evaluation indicated a marked reduction in renal damage by hydralazine therapy and even a more marked reduction by combined treatment of halofenate and hydralazine. Severe renal lesions including renal arteriolar necrosis (Nec) were observed only in hypertensive rats fed the sucrose-lard-casein diet and which received the puromycin aminonucleoside. The severity of the lesions including focal glomerulosclerosis, segmental glomerulosclerosis and global glomerulosclerosis was significantly reduced in the hydralazine, the halofenate and the combined hydralazinehalofenate treated rats along with a reduction in arteriolar thickening and necrosis.

The measured renal functions during the study clearly established the renoprotective efficacy of hydralazine hydrochloride, as well as halofenate. For example, porteinuria/creatininuria (Upr) which was induced by the puromycin aminonucleoside and enhanced by the SLC diet was significantly diminished by hydralazine hydrochloride and by halofenate. An analysis of the tabulated BUN values confirmed the renal protective action of the hydralazine hydrochloride and halofenate. It was noted, however, that no additional renal function protection occurred with combined drug therapy when compared with the significant functional renoprotective activity of hydralazine hydrochloride or halofenate.

It was concluded that the antihyperlipidemic action or other vasodilators would provide similar beneficial results. It has been suggested that other vasodilators such as prazosine hydrochloride and clonidine hydrochloride may have a tendency to reduce serum cholesterol levels in severely hypertensive hosts as indicated in the following article: Kirkendall, Walter M. et al "Prazosine and Clonidine for Moderately Severe Hypertension", J.A.M.A. Dec. 1, 1978, Volume 240, No. 23, pp. 2553-6.

The observed renoprotective activity of the vasodilator hydralazine hydrochloride apparently results from its antihyperlipidemic characteristics. It is believed that all vasodilators which exhibit antihyperlipidemic characteristics are useful as prophylactic substances against renal damage and/or failure, particularly in hosts who are not subject to severe hypertension.

Among such vasodilators having antihyperlipidemic activity are alpha-blocking agents functionally similar to hydralazine hydrochloride including endralazine, trimazosin, minoxidil and diazoxide. Additionally, vasodilators functionally similar to prazosin hydrochloride such as doxazosin, tiodazosin, phentolamine hydrochloride, phenoxybenzamine hydrochloride, benextramine, indoramine and yohimbine may be employed. A further group of vasodilators are functionally similar to clonidine hydrochloride such as methyldopa, guanabenz, guanfacine, lofexidine, and UK-No. 14,304. Combined alpha and beta blocking agents functionally similar to labetalol such as prizidolol and peroxidil may also be employed.

The following is a tabulation of recommended daily dosages of vasodilators in adult humans for renoprotective efficacy in accordance with the invention.

| VASODILATOR | DAILY DOSAGE |
| --- | --- |
| HYDRALAZINE HYDROCHLORIDE | 40-300 mg. |
| TRIMAZOSIN | 100-900 mg. |
| MINOXIDIL | 1-30 mg. |
| DIAZOXIDE (intravenous administration) | 250-500 mg. |
| PRAZOSIN | 1-40 mg. |
| PHENTOLAMINE HYDROCHLORIDE | 200-900 mg. |
| PHENOXYBENZAMINE HYDROCHLORIDE | 5-50 mg. |
| BENEXTRAMINE | 10-100 mg. |
| INDORAMINE | 40-120 mg. |
| CLONIDINE | 0.1-2.4 mg. |
| METHYLDOPA | 125-1500 mg. |
| GUANABENZ | 8-64 mg. |
| GUANFACINE | 1-35 mg. |
| LOFEXIDINE | 0.1-2.0 mg. |
| UK-14,304 | 0.2-5.0 mg. |
| LABETALOL | 200-2400 mg. |

The common conventional nomenclature for endralazine is: 6-Benzoyl-5,6,7,8-tetrahydropyrido-[4,3-C] pyridazin-3(2H)-one hydrazone; the common chemical nomenclature for doxazosin (doxazosin mesylate [Pfizer]) is: 1-(4-amino-6,7-dimethoxy-2-quinazolinyl)-4[(2,3-dihydro-1,4-benzodioxin-2-yl)carbonyl] piperazine; the common chemical nomenclature for triodazosin is: 4-amino-6,7-dimethoxy-2-[4-(5-methylthio-1,3,4-oxadiazole-2-carbonyl)-piperazin-1-yl] quinazoline hydrochloride); the common chemical nomenclature for trimazosin is: 4-(4-amino-6,7,8-trimethoxy-2-quinazolinyl)-1-piperazinecarboxylic acid 2-hydroxy-2-methylpropylester; the common chemical nomenclature for minoxidil is: 2,4-diamino-6-piperidinopyrimidine 3-oxide; the common chemical nomenclature for diazoxide is: 7-chloro-3-methyl-2H-1,2,4-benzothiadiazine 1,1-dioxide; the common chemical nomenclature for phentolamine hydrochloride is: 2[N-(m-hydroxyphenyl)-p-toluidinomethyl]imidazoline monohydrochloride; the common chemical nomenclature for phenoxybenzamine hydrochloride is: N-(2-chloroethyl)-N-(1-methyl-2-phenoxyethyl)benzylamine hydrochloride; the common chemical nomenclature for indoramin is: N-[1-[2-Indol-3-yl)ethyl]-4-piperdinyl]benzamide; the common chemical nomenclature for Yohimbine is: 17-hydroxyyohimban-16-carboxylic acid methyl ester; and the chemical nomenclature for benextramine is: N,N'-bis (6-[2-methoxybenzylamino]-n-hexyl)cystamine tetrahydrochloride monohydrate (Aldrich).

Thus, it will be seen that there is provided renoprotective treatments which achieve the various objects of the invention and which are well suited to meet the conditions of practical employment.

As various possible embodiments might be made of the present invention and since various changes might be made in the exemplary embodiments described herein, it is to be understood that all matter herein described or exemplified is to be interpreted as illustrative rather than in a limiting sense.

Having thus described the invention, there is claimed as new and desired to be secured by Letters Patent:

1. A method of treating renal damage or failure in a host in need of treatment comprising administering to said host an effective amount for treating renal failure or damage, a vasodilator having postsynaptic alpha-adrenoceptor blocking activity and having antihyperlipidemic characteristics which lower the lipid levels in the bloodstream of the host, said vasodilator being selected from a group consisting of endralazine, trimazosin, minoxidil, diazoxide, doxazosin, triodazosin, phentolamine hydrochloride, phenoxybenzamine hydrochloride, benextramine, indoramine, and yohimbine.

2. A method of treating renal damage or failure in accordance with claim 1 wherein the vasodilator is trimazosin and the trimazosin is administered to the host in substantially daily quantities totalling approximately from 100 milligrams to 900 milligrams.

3. A method of treating renal damage or failure in accordance with claim 1 wherein the vasodilator is minoxidil, and the minoxidil is administered to the host in substantially daily quantities totalling approximately from one milligram through 30 milligrams.

4. A method of treating renal damage or failure in accordance with claim 1 wherein the vasodilator is diazoxide, intravenously administered to the host in substantially daily quantities totalling approximately from 250 milligrams through 500 milligrams.

5. A method of treating renal damage or failure in accordance with claim 1 wherein the vasodilator is phentolamine hydrochloride, and the phentolamine hydrochloride is administered to the host in substantially daily quantities totalling approximately from 200 milligrams through 900 milligrams.

6. A method of treating renal damage or failure in accordance with claim 1 wherein the vasodilator is phenoxybenzamine hydrochloride, and the phenoxybenzamine hydrochloride is administered to the host in substantially daily quantities totalling approximately from 5 milligrams through 50 milligrams.

7. A method of treating renal damage or failure in accordance with claim 1 wherein the vasodilator is benextramine, and the benextramine is administered to the host in substantially daily quantities totalling from approximately 10 milligrams through 100 milligrams.

8. A method of treating renal damage or failure in accordance with claim 1 wherein the vasodilator is indoramine, and the indoramine is administered to the host in substantially daily quantities totalling approximately from 40 milligrams through 120 milligrams.

* * * * *